(12) United States Patent
Melbye et al.

(10) Patent No.: US 6,195,850 B1
(45) Date of Patent: Mar. 6, 2001

(54) CLOSURE SYSTEM FOR DISPOSABLE ABSORBENT ARTICLE

(75) Inventors: William L. Melbye; Jayshree Seth, both of Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 09/524,802

(22) Filed: Oct. 14, 1999

Related U.S. Application Data

(62) Division of application No. 08/944,169, filed on Oct. 6, 1997, now Pat. No. 6,051,094.

(51) Int. Cl.[7] .......................... A44B 18/00; A61F 13/56; B32B 31/18
(52) U.S. Cl. ................. 24/304; 24/306; 24/442; 24/451
(58) Field of Search .............. 24/442, 304, 306, 24/451

(56) References Cited

U.S. PATENT DOCUMENTS

| | | | |
|---|---|---|---|
| 4,012,544 | * | 3/1977 | Richards ................. 24/306 |
| 4,653,582 | * | 3/1987 | Ehrenfried ............... 24/442 |
| 5,108,384 | * | 4/1992 | Goulait ................... 604/390 |
| 5,537,722 | * | 7/1996 | Niederhofer et al. ....... 24/304 |
| 5,605,735 | * | 2/1997 | Zehner et al. ............ 428/100 |
| 5,624,429 | * | 4/1997 | Long et al. .............. 24/306 |

FOREIGN PATENT DOCUMENTS

0250175 * 12/1987 (EP) ........................... 24/442

* cited by examiner

*Primary Examiner*—Victor N. Sakran
(74) *Attorney, Agent, or Firm*—Gary L. Griswold; Robert W. Sprague; William J. Bond

(57) ABSTRACT

A closure system and method of making a closure system for a disposable article. A substantially continuous closure system web is provided. One face of the web is provided with first fastening region at terminal end portion(s) of the web. A second fastening region, engagable with the first fastening region, is provided on a second face of the web in a region adjacent the terminal end portion(s). The closure system tab elements are cut from the web and attached to a second web, used in producing the disposable article, at longitudinally spaced locations. This second web is then cut at transverse cut lines separating the closure system tab element into two functional elements. A first functional element has a fastening tab portion and the second functional element has an attachment portion, The attachment portion of one closure system tab element interacts with a fastening tab portion of an adjacent closure system tab element to form a functional closure system on a disposable article made using the second web.

40 Claims, 14 Drawing Sheets

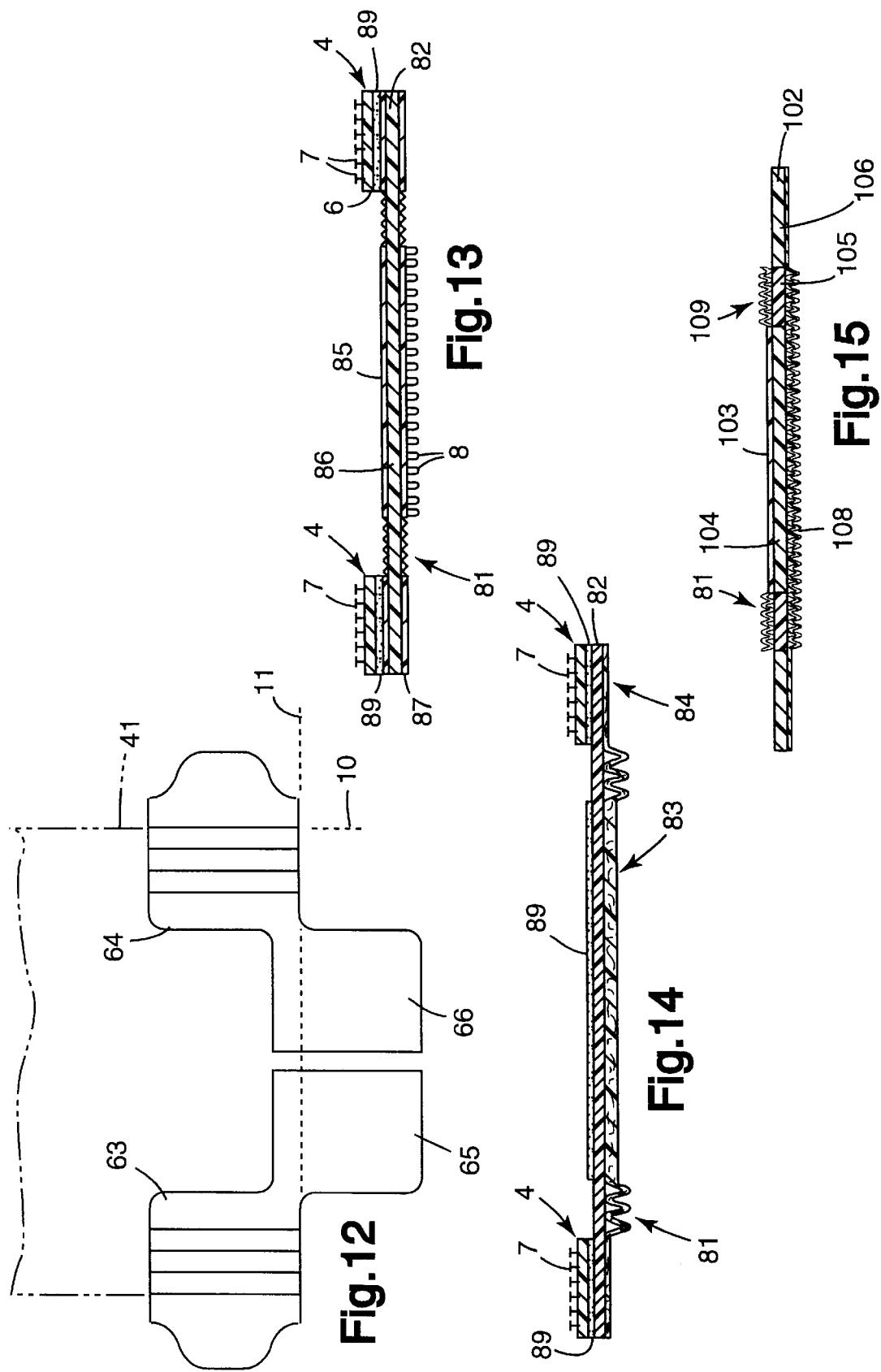

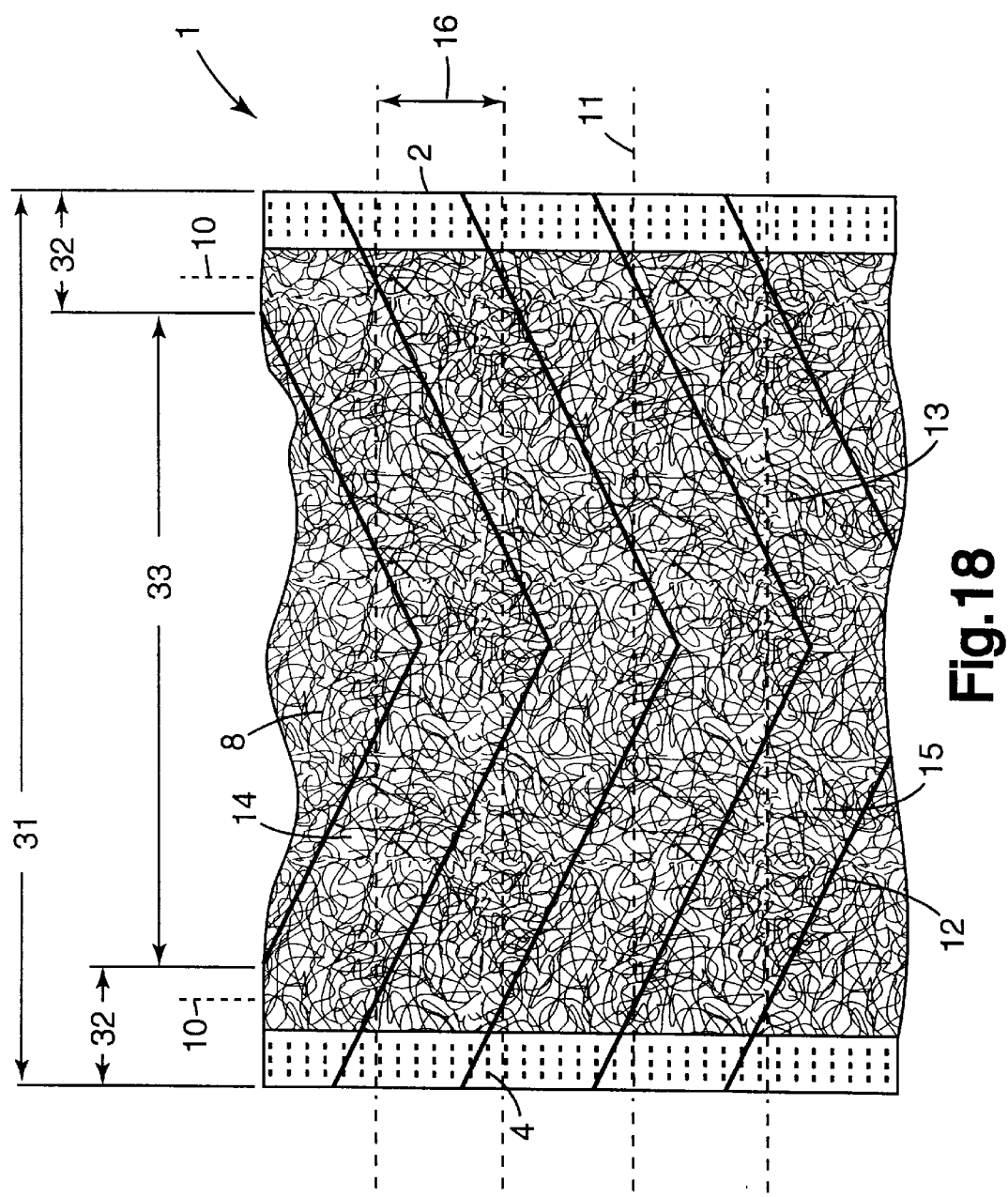

CLOSURE SYSTEM FOR DISPOSABLE ABSORBENT ARTICLE

This is a divisional of application Ser. No. 08/944,169 filed Oct. 6, 1997, now U.S. Pat. No. 6,051,094.

BACKGROUND AND FIELD OF THE INVENTION

The present invention relates to a closure system for a disposable absorbent article, particularly multifunctional closure systems attachable to the waistband portions of the disposable absorbent article.

In the field of disposable absorbent articles, typically disposable diapers and adult incontinent articles, closure systems are provided which generally are formed using pressure sensitive adhesive fastening tabs or mechanical fastening tabs. These tabs are generally attached to the disposable absorbent article at corner portions at at least one end of the article, e.g., a diaper. The typical fastening tabs have one end which is permanently bonded to the absorbent article and a second free end which is available for the user to removably attach to the opposing end of the article to effect closure. The opposing end of the absorbent article typically is provided with a mating attachment surface. In the case of pressure sensitive adhesive fastening tabs, the mating attachment surface typically is a reinforcement film or other material which is applied to the inside or outside face of the outer liquid impermeable layer of the disposable absorbent article. In the case of a mechanical fastening tab, the mating attachment surface is a loop fastening material which must be placed on the outside face of the liquid impermeable outer cover layer of the disposable absorbent article. In either case, the mating attachment surface is typically provided by applying a separate discrete element to the absorbent article. This could be a pressure sensitive adhesive element or a non-adhesive coated element bonded by other means such as hot melt adhesive or thermal welding. In certain extreme cases, the entire outer face of the disposable absorbent article can be provided with a suitable mating attachment surface for the fastening tab second free end, however this can be excessively costly. The fastening tab itself is also applied as a separate and discrete element to the corner of the disposable absorbent article, generally at the back end region. Generally, this permanent attachment of the fastening tab is made by a pressure sensitive adhesive applied at one end of the fastening tab with the other second end of the fastening tab provided with a suitable pressure sensitive adhesive or mechanical fastening element for releasable attachment and closure of the absorbent article. The fastening tab can be applied as a separate piece cut from a roll which can be laminated with other suitable materials, such as a release tape, during the manufacture of the diaper. Alternatively, the fastening tab can be provided with other suitable components in a pre-laminate form which also is cut from a continuous roll. These closure systems are highly effective but can be complicated, particularly when they are laminated on the diaper line and/or additional functionality is incorporated into the fastening tab, such as elasticity.

It has also been proposed in the patent literature that suitable belt means could be provided with attachment elements at the opposing ends of the belt to provide a closure system for use with a disposable absorbent article. Belts can address some of the issues regarding separate tab fasteners as some only require the use of a single laminate or the like which can be securely or releasably attached to a diaper absorbent pad or the like. However the use of two interconnecting belts have also been proposed. In U.S. Pat. Nos. 3,847,702 and 3,561,446, an inextensible belt material is provided both to the front and back ends of a disposable diaper. Each belt extends across the full width of the diaper and both belts are provided at the terminal ends with a pressure sensitive adhesive region which adhesive is covered until use with a release tape. When the diaper is closed, one belt is attached to some portion of the second belt at the opposite end of the diaper, and the adhesive on the terminal ends of the second belt is generally attached to the diaper on the diaper face opposite that provided with the first belt. These belts prevent inelastic deformation of the waistband region of the diaper during use. However, this two-belt system would be similar in manufacturing complexity to the use of tab fasteners.

French Pat. Nos. 2,586,558, 2,725,879, and PCT Publ. No. 94/26224 teach the use of only one inextensible belt which single belt can be attached to the front or rear ends of the diaper, either permanently or by refastenable mechanical fastening elements. When the diaper is refastenably attached to the belt, the belt can be repeatedly. In these patent documents, the belt generally wraps around the wearer and secures to itself with the diaper being releasably attached to the belt at least at one end of the diaper, and either releasably or permanently attached to the belt at the opposing end of the diaper. A similar approach is proposed in U.S. Pat. No. 4,964,860, and PCT Appln. No. 91/08725 where a reusable belt with mechanical fastening elements is used with a disposable diaper provided with mating mechanical fastening elements. These belts can be relatively easy to incorporate onto a diaper but lack the ease of use of a fastener tab closure system for the end user.

In EP Appln. No. 528282, a permanent integral waistband is provided on a diaper which waistband could be stretchable. The waistband is on one end of the diaper and wraps around the wearer's waist and attaches to itself forming a belt. Both the waistband and the front portion of the diaper are provided with suitable interengagable attachment elements 44 and 50 which could be any variety of attachment means including pressure sensitive adhesives, cohesive adhesives, and mechanical fasteners. The front portion of the diaper would attach to the waistband portion. This patent attempts to combine some of the benefits of a single belted system with those of a tab fastening closure system.

In U.S. Pat. No. 5,593,401, a bridging type element is provided at one end region of a diaper as a separate element to which may be attached two conventional fastening tabs at either end. The bridge strip has a secured side and an unattached side and is generally described as being elasticized. This bridge strip would require a separate attachment step and associated apparatus in order to be integrated into the disclosed conventional diaper constructions. This is similar to the above two belt systems but is more complicated in terms of its construction and manufacture.

Elasticized waist elements which may have attached fastening tabs that then releasably attach to a front panel portion of a diaper are disclosed in U.S. Pat. No. 4,998,929, and PCT Publ. Nos. WO 96/32083, and WO 95/22951. An elastic type belt element which wraps around the entire waist of the wearer and which is provided with inter-engaging mechanical fastening elements at its terminal ends is disclosed in U.S. Pat. No. 5,607,416. In all the above patent documents, there is a separate and distinct elastic element with the terminal edges generally including an attachment element such as a pressure sensitive adhesive or a mechanical fastening element which attaches to the elastic belt as per U.S. Pat. No. 5,607,416 or to a suitable attachment mechanism on the other end portion of the diaper or like disposable absorbent article.

The use of two or one belt closure systems that wrap around one end of a diaper or the entire waist of the wearer, respectively, are desirable from a number of perspectives. The belt can be used with the closure system in a manner that provides other functionality such as elasticity or inextensibility that is actively integrated with the closure system. However, the means proposed for providing these belt and closure elements generally requires a number of separate attachment steps on the manufacturer's line.

The invention is directed at addressing the manufacturing complexities of multicomponent closure systems by enabling the provision of an effective closure system by a single attachment step which can also provide additional desired functionality such as inextensible belt elements, extensible belts or bands, elasticity, and the like. The invention is also directed at a method of providing a diaper closure system and optionally a belt system on a diaper line by the use of a single closure system laminate.

BRIEF DESCRIPTION OF THE INVENTION

The invention comprises a closure system and a method of forming a closure system for a disposable absorbent article. The method comprises the steps of providing at least one substantially continuous web capable of forming a portion of a disposable absorbent article. The web has a first width dimension defining two side edges and an indefinite length dimension. A closure system web is also provided comprising at least one backing having a first face and a second face. The closure system web has a second width dimension generally greater than the first width dimension and an indefinite length. The first face of the closure system web is provided with at least one first fastening region at at least one terminal end portion of the closure system web. At least one second fastening region is provided on the second face of the closure system web in at least the second portion adjacent the terminal end portion provided with the first fastening region. Closure system tab elements are cut from the closure system web, which tab elements have a definite length dimension. The closure system tab elements have at least one fastening tab portion, comprising the at least one first fastening region on the terminal end portion, and an attachment portion comprising the second portion having the second fastening region.

The closure system tab elements are then attached to the at least one substantially continuous web at regular spaced intervals along the indefinite length dimension in a continuous manner. The at least one continuous web is then cut along cut lines transverse to the indefinite length dimension to form discrete disposable absorbent articles. The transverse cut lines are such that they bisect the closure system tab elements along the tab element definite length dimension, so that the fastening tab portion is on a first side of the transverse cut line and the attachment portion is on a second opposing side of the cut line. This provides fastening tab portions on a first end of one absorbent article and an attachment portion on a second end of an adjacent absorbent article.

A closure system of the invention is used on a disposable absorbent article having a first width dimension defining two side edges and two end edges. The closure system comprises at least one fastening tab having a backing. A first face of the fastening tab backing is provided with at least one first fastening region at at least a first end. At least one second fastening region is provided on a first face of an attachment portion having a backing. The attachment portion has a top edge and a bottom edge. Preferably at least a discrete portion of the attachment portion top edge is laterally coextensive with a portion of a first end edge of the disposable absorbent article. A corresponding and coextensive discrete portion of a bottom edge of the at least one fastening tab is also preferably laterally coextensive with a second end edge of the disposable absorbent article. At least a portion of the attachment portion top edge is laterally coextensive with the bottom edge of the at least one fastening tab which both preferably form a portion of, or are adjacent to, end edges of the disposable absorbent article. The respective backings of the at least one fastening tab and the attachment portion are identical, at least at an area adjacent the two discrete coextensive edge portions of the at least one fastening tab and the attachment portion.

BRIEF DESCRIPTION OF THE DRAWINGS

FIG. 12 is a top perspective view of a FIG. 11 embodiment as it would be applied to a web 41 forming a disposable absorbent article.

FIGS. 13–15 are side cross sectional views of further embodiments of closure system webs in accordance with the present invention.

FIG. 18 is a top perspective view of a further embodiment of a closure web in accordance with the present invention.

DESCRIPTION OF THE PREFERRED EMBODIMENTS

The instant invention is directed at providing a fully functional closure system for a disposable absorbent article, integrated with the process of forming the disposable absorbent article, by attachment of unitary closure system tab elements. The tab elements are cut from a continuous closure system web product and then attached to a continuous or substantially continuous absorbent article web from which discrete disposable absorbent articles are eventually cut. These closure system tab elements provide both the fastening tabs and a suitable mating attachment surface for the disposable absorbent articles. However the fastening tabs and mating attachment surface of a single closure system tab element end up on different absorbent articles when the absorbent articles are cut from the absorbent article web.

Figure 1:
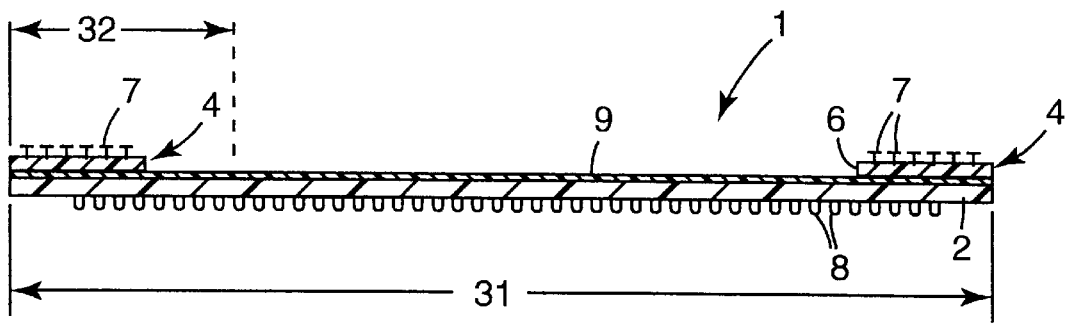
FIG. 1 is a side cross sectional view of a first embodiment of a closure system web used in the present invention.

A first embodiment of a closure system web product, in cross section, is shown in FIG. 1, which comprises a laminate of a backing layer (2) having a first face provided with a pressure sensitive adhesive layer (9). Adhesive layer (9) is used for eventual attachment of the closure system tab elements to the disposable absorbent article web. Attached to the backing (2) at terminal end portions are first fastening regions. In the FIG. 1 embodiment the first fastening region is provided by a hook mechanical fastening material (4) formed from hook mechanical fastening elements (7) projecting from a hook backing (6). However the fastening region can be formed directly on the backing (2) rather than being attached as a separate element by, for example, use of an adhesive as shown in FIG. 1. The second face of the backing (2) in FIG. 1 is provided with second fastening region comprising a mating loop mechanical fastening material (8) which would engage with the hook mechanical fastener material (4). These two mating fastening materials together from a unitary closure system when applied to a diaper web, or the like, in accordance with the invention.

Figure 2:
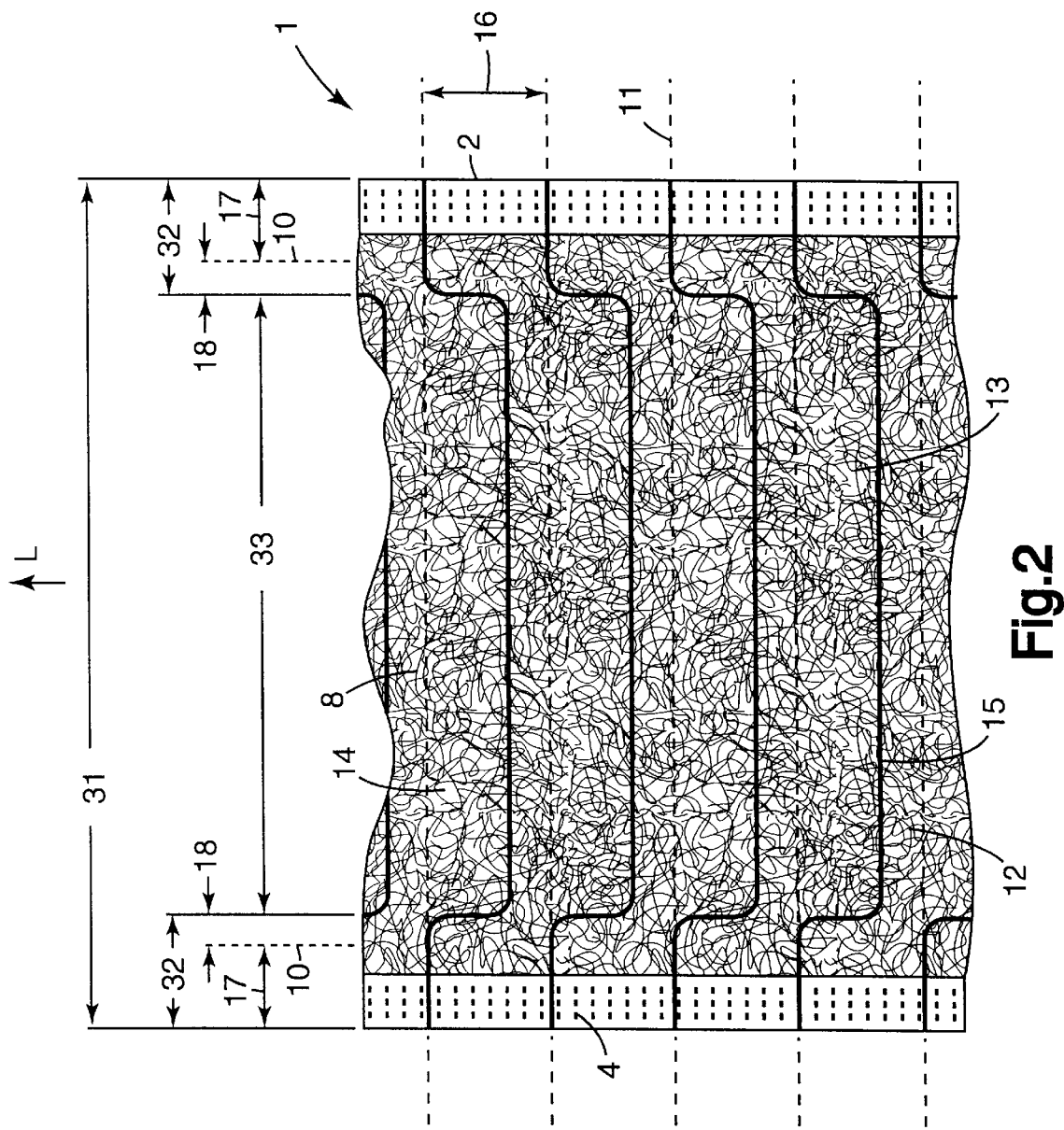
FIG. 2 is a top perspective cut away view of a portion of a closure system web such as shown in FIG. 1.
Figure 8:
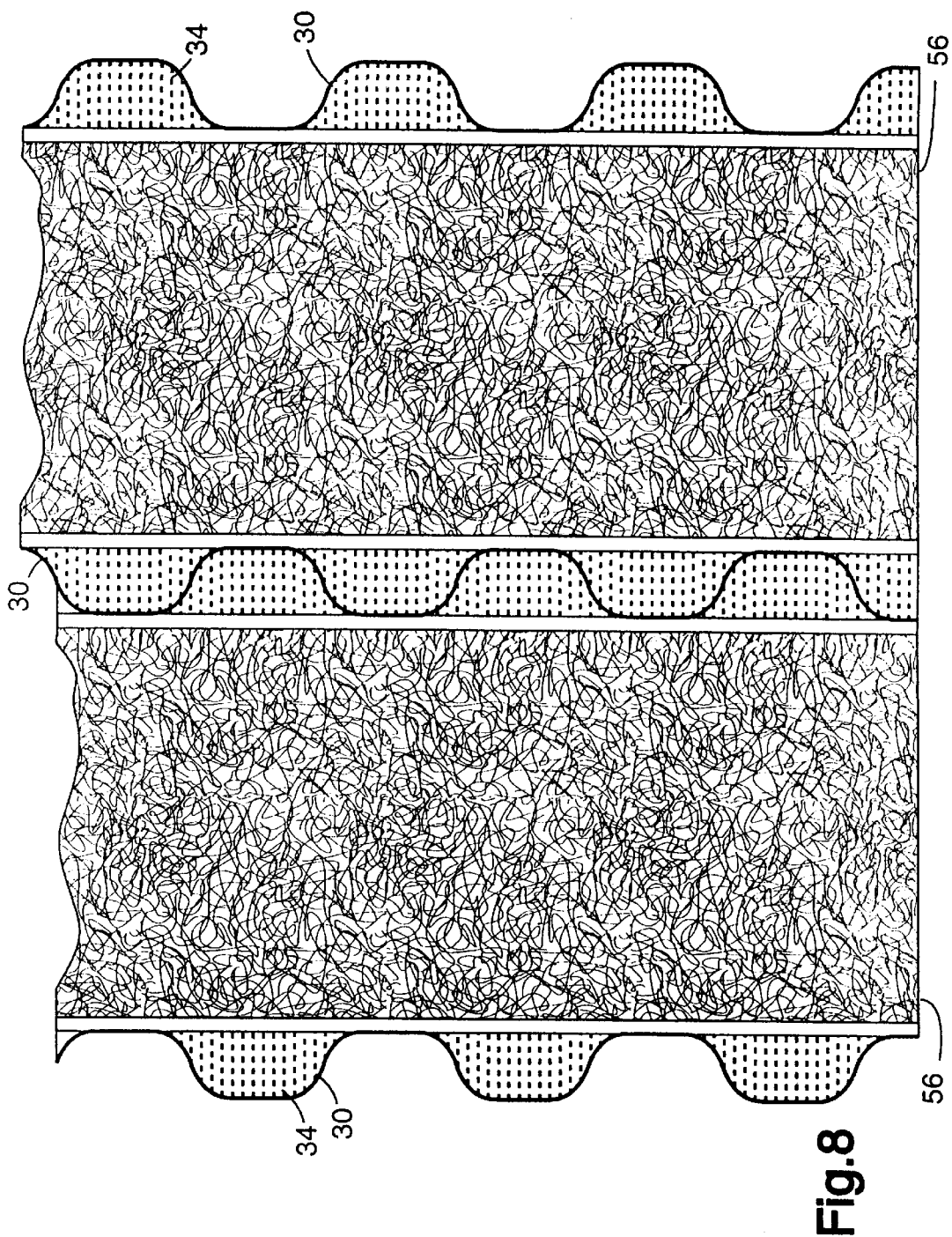
FIG. 8 is a top perspective view of further embodiment of a closure system web in accordance with the present invention having a double width.
Figure 11:
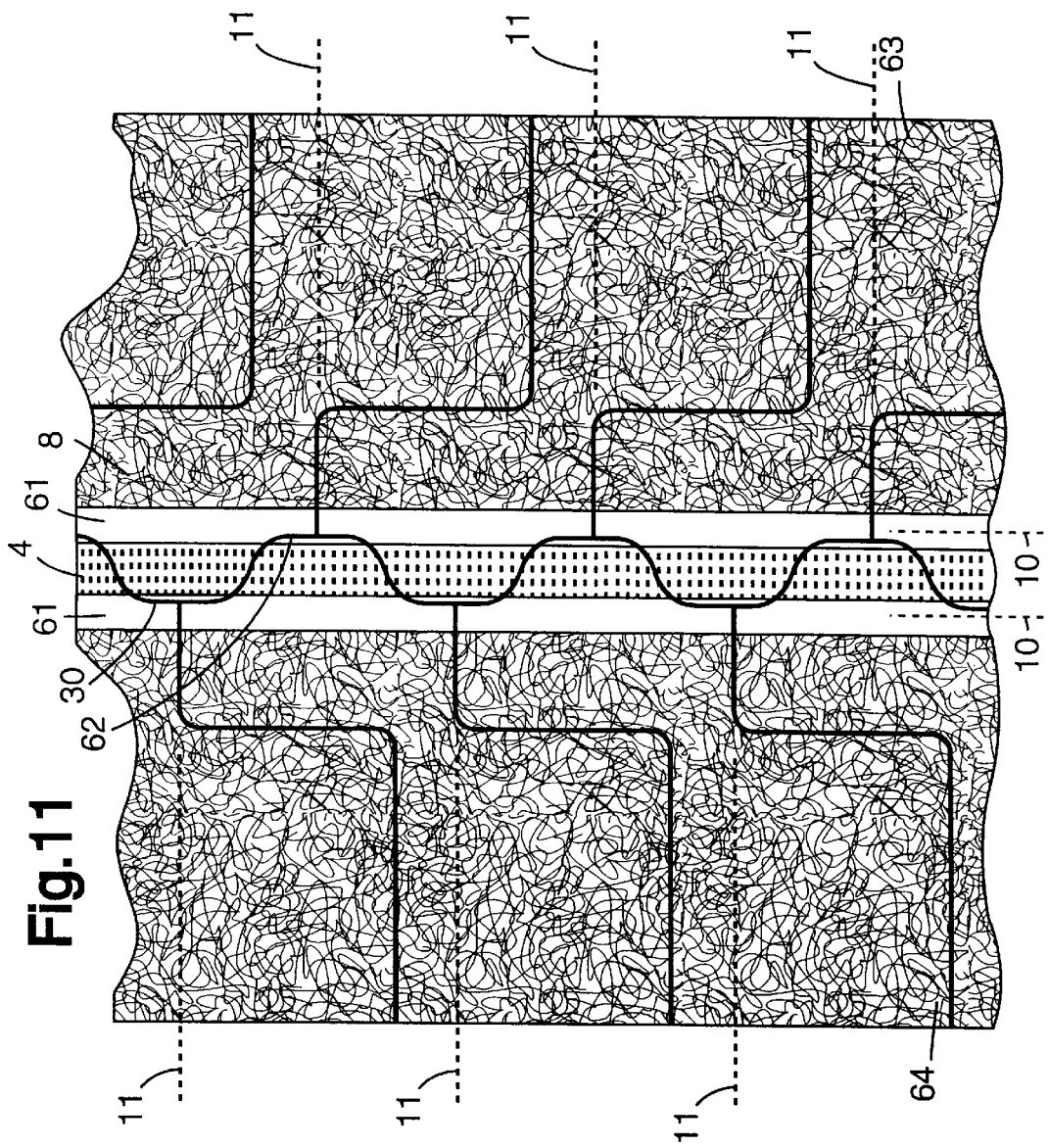
FIG. 11 is a top perspective view of a further closure system web in accordance with the present invention.

The closure system tab elements (14) are cut from the continuous closure system web (1) along cut lines (15) as shown in FIG. 2. The closure system web (1), and the closure system tab elements (14) cut therefrom, have a width dimension (31) which is divided into terminal end portions (32) and a second portion(s) (33). Although the terminal end portions (32) can be at the side edges of the closure system web, as shown in FIG. 2, they can also be provided at intermediate regions of a closure system web as shown in FIGS. 8 and 11. The closure system web (1), generally has an indefinite length direction (L), however, the closure system tab elements (14) cut from the web (1) generally have a definite length dimension (16) which is preferably constant across the majority of the width (31) of the closure system tab element (14), and is preferably constant over at least the entire second portion (33).

If closure system tab elements (14) vary in length (16) across their width, two separate cut lines must be provided to define the top and bottom of adjacent closure system tab elements. This requires material waste or selvage between the two separate cut lines. If a single tab element cut line defines both the top and bottom of two adjacent tab elements (14), there is no waste, but the length (16) of the tab elements will be constant across the width of the tab element along the shared boundary defined by the single tab element cut line (except possibly in the special case where the tab element cut lines are parallel to the length direction, in which case the width would include the length of the cut line). However, inevitably the tab element cut line is not straight and does vary in the length direction of the continuous web so that the terminal end portions (32) are offset from the second portion (33) in the length dimension. The average offset is at least 10 percent of the maximum length of the terminal end portions preferably at least 50 percent.

On the terminal end portion (32) is generally provided the first fastening region, which in the case of FIG. 2 is hook mechanical fastening material (4) which engages with a mating second loop mechanical fastening material (8) on an attachment portion of the second portion (33). In FIG. 2 the second fastening region forming the attachment portion is the loop material (8).

Figure 16:
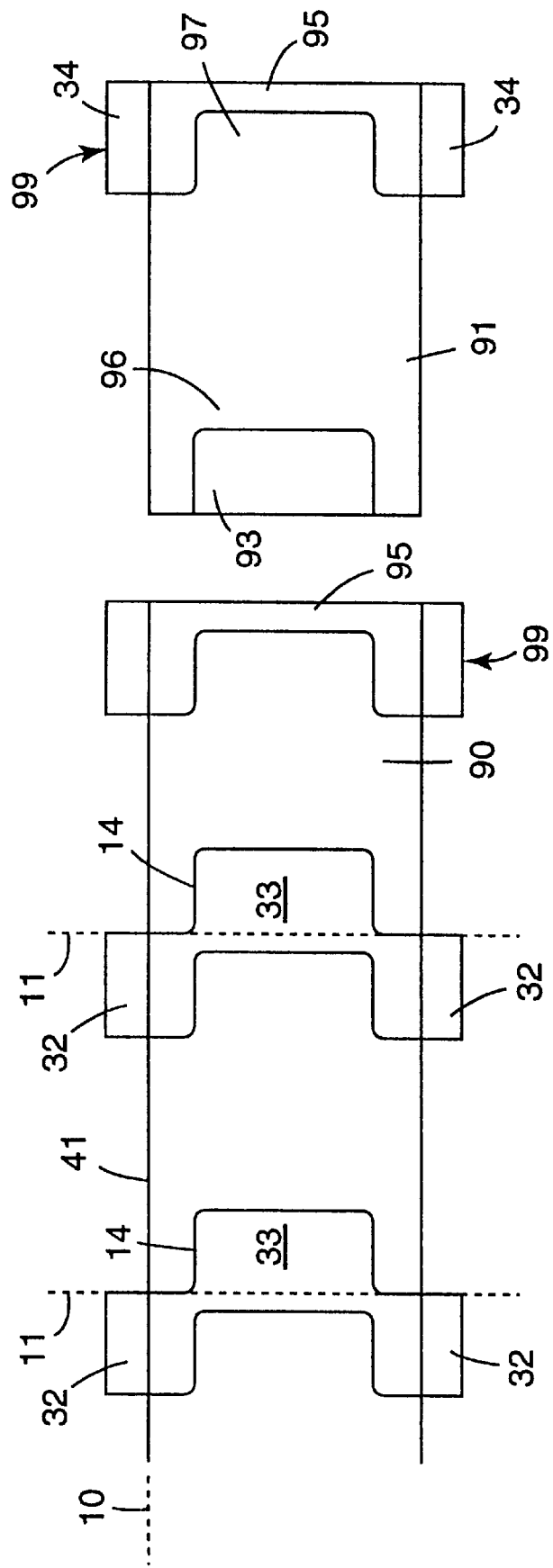
FIG. 16 is a top perspective schematic view of how the closure system webs of the present invention would be cut out and applied as tab elements in the formation of disposable absorbent articles from a continuous web 41.

The closure system tab elements (14) when cut from the closure system web (1) provide unitary structures which are attached to a continuous or substantially continuous web used in forming the absorbent articles at a location having the above first width. As shown in FIG. 16, the outer backsheet web of a diaper can form the continuous web. A continuous web, as shown in FIG. 16, is either assembled, or will be assembled, with other components to form a continuous disposable absorbent article web. From this disposable absorbent article web discrete disposable absorbent articles are cut. For example, these other components, in addition to the backsheet web, can include an absorbent batt material, a fluid permeable top sheet, a fluid transport layer or similar continuous or substantially continuous web elements which are conventionally integrated into the manufacture of a disposable absorbent article. Also, other discrete elements can be attached to the continuous web(s) such as further tab elements, elastics such as leg or waist elastics, liquid barriers, reinforcement elements, or the like.

The continuous web as shown in FIG. 16 is a backsheet web but other continuous webs could be used for attachment of the closure system tab elements; for example, nonwoven cover sheets, liquid pervious topsheets, or the like. Also, the continuous or substantially continuous web to which the closure system tab elements is attached could be nonplanar, laminated to other webs, or composites created by a lamination of multiple discrete components. A substantially continuous web can also be used having short regions of discontinuity creating web elements that generally are sequentially arranged and continuously supported, at least in the region where the closure system tab elements are attached. However, in this embodiment, when the closure system tab elements are attached to the discrete continuously supported web elements, the web elements and the attached closure system tab elements will form a continuous web at least in the region between where the closure system tab elements are attached and the discrete absorbent articles are cut and/or the closure system tab element are bisected.

In FIG. 2, the numeral (10) indicates the side edges of the at least one absorbent article continuous web (41) to which the closure system tab elements (14) are attached at discrete longitudinally displaced locations along the length of an at least one absorbent article continuous web (41), as shown in FIG. 16. The continuous web (41) is then cut into discrete absorbent articles along transverse cut lines (11) which transverse cut lines generally also bisect or cut the closure system tab elements (14) as shown, e.g., in FIGS. 2 and 16. However, it is possible to bisect the closure system tab element before cutting the discrete absorbent article by, for example, bisecting the closure system tab elements as part of a continuous web and attaching these discrete elements to a further web from which the discrete absorbent articles are eventually formed. When the discrete absorbent articles are cut, the terminal end portions (32) and a portion of the second portion (33) forming a bridging element or band (95 or 12) remain attached to a first disposable absorbent article (90) with a majority of the second portion (33) remaining on an adjacent disposable absorbent article (91), forming the attachment portion (93 or 13).

The terminal end portions (32) have a first end (17) which projects outwardly beyond the side edges (10) of the disposable absorbent article and a second end (18), which remains permanently attached to the disposable absorbent article web (41). At least a portion of the first end (17) contains the first fastening region, such as the hook material (4) in FIG. 2. The mating loop material (8) on the second portion (33) attachment portion (93 or 13), when attached to continuous web (41), forms the mating mechanical fastening surface on the adjacent absorbent article (91) which in conjunction with the next downweb closure system tab element terminal end portions (32) forms a unitary closure system on a disposable absorbent article (90).

Generally, the attachment portion (93) is attached to the front region (96) of a disposable absorbent article or the like. The terminal end portions (32) containing the first fastening region are attached to a back portion (97) of the disposable absorbent article. However, the front and back portions are determined by how the article is attached, which can be determined by the user. As such, the front portion could be used as the back portion if the absorbent article is generally symmetrical and the user so chooses.

The terminal end portions (32), provided generally on only a first side of the traverse cut line (11), form fastening tab portions (99) on a disposable absorbent article. These fastening tab portions, as shown in FIGS. 2 and 16, can be interconnected by, or include, a portion of the second portion (33). When these portions of the second portion (33) interconnect two fastening tab portions, they act as a bridging portion or band (12 or 95) around a front or back peripheral edge of the disposable absorbent article (91). Consequently, when the fastening tab portions (99) are attached to the attachment portion (13 or 93) a continuous band is formed around the peripheral edge of the disposable absorbent article formed by the front portion (96) and the back portion (97). This bridging portion or band (12 or 95) can be in whole or in part inextensible, extensible and/or elastic depending on the material forming the backing layer (2).

The bridging element or band (12 or 95) can provide functionality such as inextensibility if a suitable backing (2) is selected. Inextensibility is desirable in that the garment, such as a diaper, can permanently stretch when it is worn. This stretching results in a loose fit and possibly leakage, or even the diaper falling off. If a continuous inextensible band is provided around the diaper this stretching can be minimized or eliminated. Elasticity in the bridging element (12 or 95) can also address stretching by positively engaging the wearer around the waist, providing an elastic recovery force. In this case, all or a portion of the backing (2) is provided to be elastic, and the closure system tab elements (14) are applied in a manner as is conventional for a waist elastic or like elastic components.

FIG. 16 is a schematic illustration of a continuous web, of the disposable absorbent article (41), to which is attached the closure system tab elements (14) such as depicted in FIGS. 1 and 2. The terminal end portions (32) when cut from the attachment portion (13 or 93) of the second portion (33) by the transverse cut line (11) forms two fastening tab portions (99), connected by a bridging element (95), at the terminal side edges (10) of the disposable absorbent article (91) cut from the web (41). The second portion (33) attachment portion (13 or 93) forms the mating attachment surface second fastening region to which the fastening tab portion (99) first fastening region adheres. The transverse cut line (11) bisects the closure system tab element (14) along its definite length dimension (16) such that a fastening tab portion (99) and bridging element (12 or 95) is on one side of the traverse cut line (11), and the attachment portion (13 or 93) is on the second opposing side of the traverse cut line. A unitary closure system is formed on a single disposable absorbent article (91) by the respective fastening tab portions (99) on a first side of the transverse cut line of a first closure system tab element (14) in combination with the adjacent attachment portion (93) cut from the second opposing side of a second adjacent closure system tab element (14).

Generally, the fastening tab portion maximum length is from 2 to 10 cm long, preferably from 2 to 5 cm long and from 2 to 20 cm wide, preferably from 5 to 15 cm wide based on the size of the article. However, the first fastening region can be from 0.5 to 5 cm long on average, preferably from 1 to 4 cm long or arranged to provide a cross sectional area of from 0.25 to 25 $cm^2$, preferably from 1 to 10 $cm^2$. The portion of the fastening tab portion permanently attached to the article includes the terminal end portion (32) second end and possibly a portion of the second portion (33). Overall, the minimum width of the fastening tab portion (99) second end permanently attached to the diaper is from 1 to 5, preferably from 2 to 4 cm.

The overall length of the attachment portion (13, 93) is preferably at least 40 to 95 percent of the length of the first fastening region, preferably 60 to 90 percent. The length of the bridging element can vary across its width, as can the length of the attachment portion. The average length of the attachment portion can range from 5 to 100 cm, preferably from 10 to 50 cm. Overall, the maximum length (16) of the closure system tab element can vary as required and could be from 10 to 200 cm, preferably from 20 to 100 cm. The bridging member length can be zero, or close to zero, where it provides no functionality as a continuous belt element. However if the bridging element functions as an elastic band or an inextensible band or the like, it is generally has a minimum length of at least 0.5 cm and generally at least 1 cm to 5 cm long. The bridging element average length generally is less than the average length of the attachment portion. Preferably, the average length of the bridging element is less than 40 percent of the average length of the attachment portion. The bridging element and the attachment portion, if combined, will generally form a rectangular shape, when the tab elements are separated by a single cut line in the second portion. As such, the bridging element and the attachment portion are generally negative inverted mirror images of each other.

Figure 3:
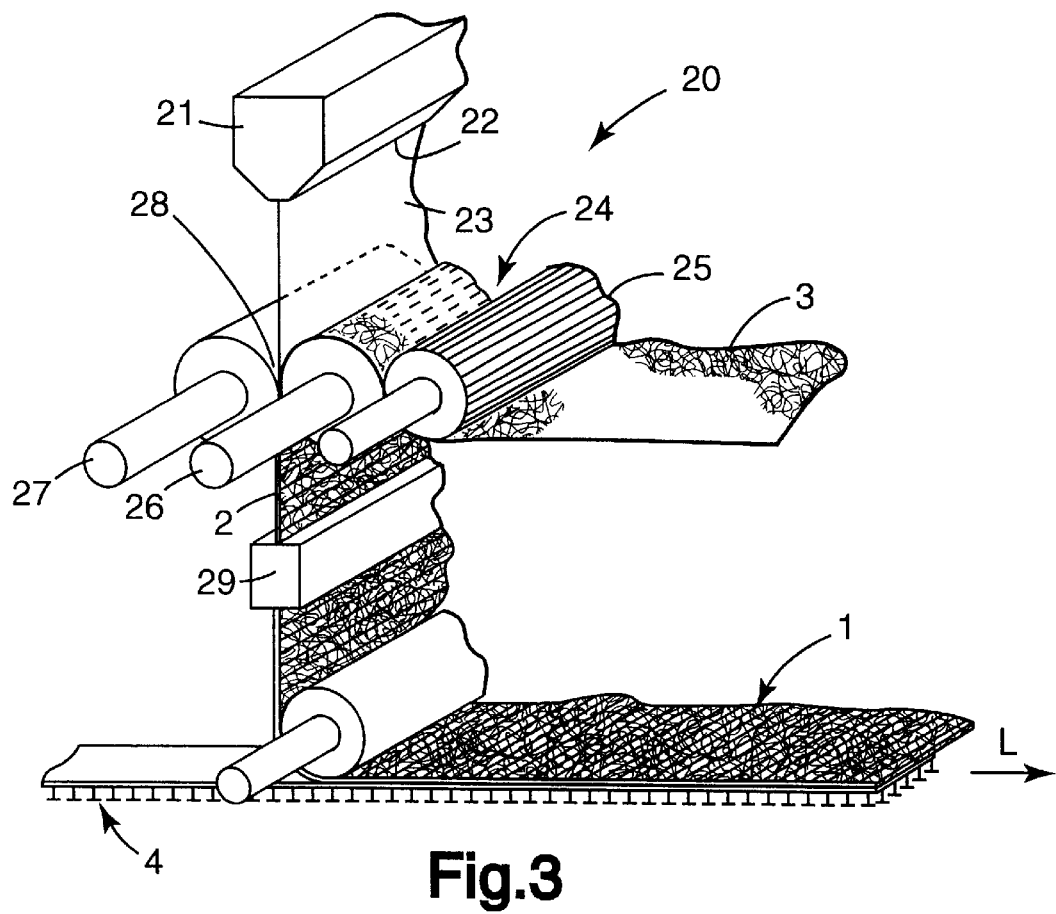
FIG. 3 is a cut away schematic view of an apparatus for forming the closure system web of the invention such as shown in FIGS. 1 and 2.

FIG. 3 illustrates a method for forming the closure system web of FIGS. 1 and 2 having hook and loop fastening regions using the methods substantially described in U.S. Pat. No. 5,256,231 to form the loop fastening region. By this method, a sheet of fibers (3), which can be a non-woven web, used to form the loop material (8) is fed by conventional means, such as from a supply roll or directly from a web-forming process, between a pair of mutually parallel intermeshing rollers (25 and 26) which are provided with intermeshing teeth. These teeth intermesh in the manner of gear-teeth with ridges on one roll fitting into valleys on the adjacent roll, and visa versa. As shown in FIG. 3, these intermeshing teeth can be aligned radially along the length of rollers (25 and 26), however, these gear teeth could also be arranged in numerous other regular intermeshing patterns including circumferentially extending gear teeth along the diameter of rollers (25 and 26), or in mating geometric patterns such as diamonds, hexagons, squares, circles, or any other regular or irregular pattern where the peak portions of a pattern on one roll intermesh with the valley portions of a pattern on the adjacent roll. Upon exiting from the nip (24) formed by rolls (25 and 26), the sheet of fibers is retained along the periphery of the roll (26) such as by applying web tension, vacuum, differentially heating roll (26) and/or roughing the surface of roll (26). At this point, the sheet of fibers (3) is maintained in its deformed or corrugated state and is given dimensional stability by joining with a dimensionally stable web material such as a film or a dimensionally stabilized woven or non-woven fabric. Alternatively the corrugated sheet of fibers can be made to be elastic or extensible by being joined to an elastic or extensible web material which web material can form the closure system web backing (2).

As shown in FIG. 3, the corrugated loop material (8) retained on the surface of roll (26) is directly joined to a molten extruded film material (23) which is formed in a die provided with a die opening (22). The extruded film material (23) being still in a molten, or semi-molten condition is sufficiently soft to allow the sheet of fibers (3) corrugated on roll (26) to become embedded within the extrudate. This provides secure bonding and also dimensional stability or other properties based on the properties of the film backing (23) and any further layers provided (not shown). The backing roll (27) forms a nip with roll (26), which roll (27) is generally a cooled, smooth roll. The nip pressure is preferably substantially constant across the width of the laminated web material formed at least by the corrugated sheet of fibers (8) and the extrudate (23). Additional cooling rollers could be provided or the laminate could be further wrapped around roller (27) to provide further cooling as desired. The laminate backing (2) is then further coated with adhesive (9) using an adhesive coater (29), which can be a pressure sensitive adhesive. Adhesive (9) can then be used to adhesively bond the mechanical fastening material (4) to the backing (2). The mechanical fastening material (4) can also be previously adhesively coated and then joined with the laminate web backing (2) or attached by other mechanisms including sonic bonding, point bonding, sewing, or the like.

If a pre-formed web material is provided as the backing (2), the nip (28) formed between rolls (26 and 27) is preferably heated so as to thermally bond the sheet of fibers (8) to the pre-formed backing materials, such as by providing rolls (26 or 27) with heating elements such as an oil heated roll, a water heated roll, an induction heated roll, or an ultrasonic horn.

Figure 4:
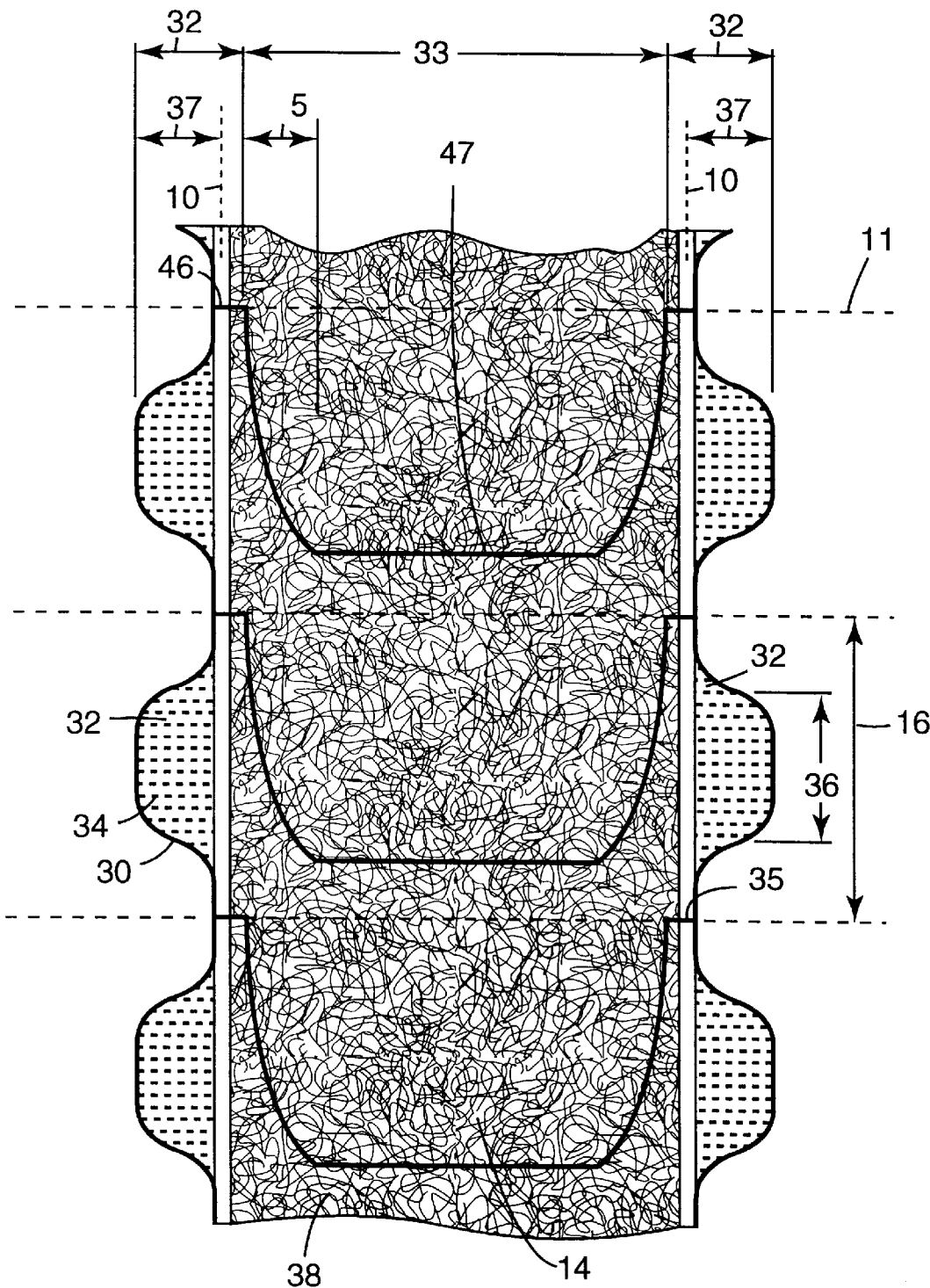
FIG. 4 is a top perspective view of a second embodiment of a closure system web in accordance with the present invention.
Figure 6:
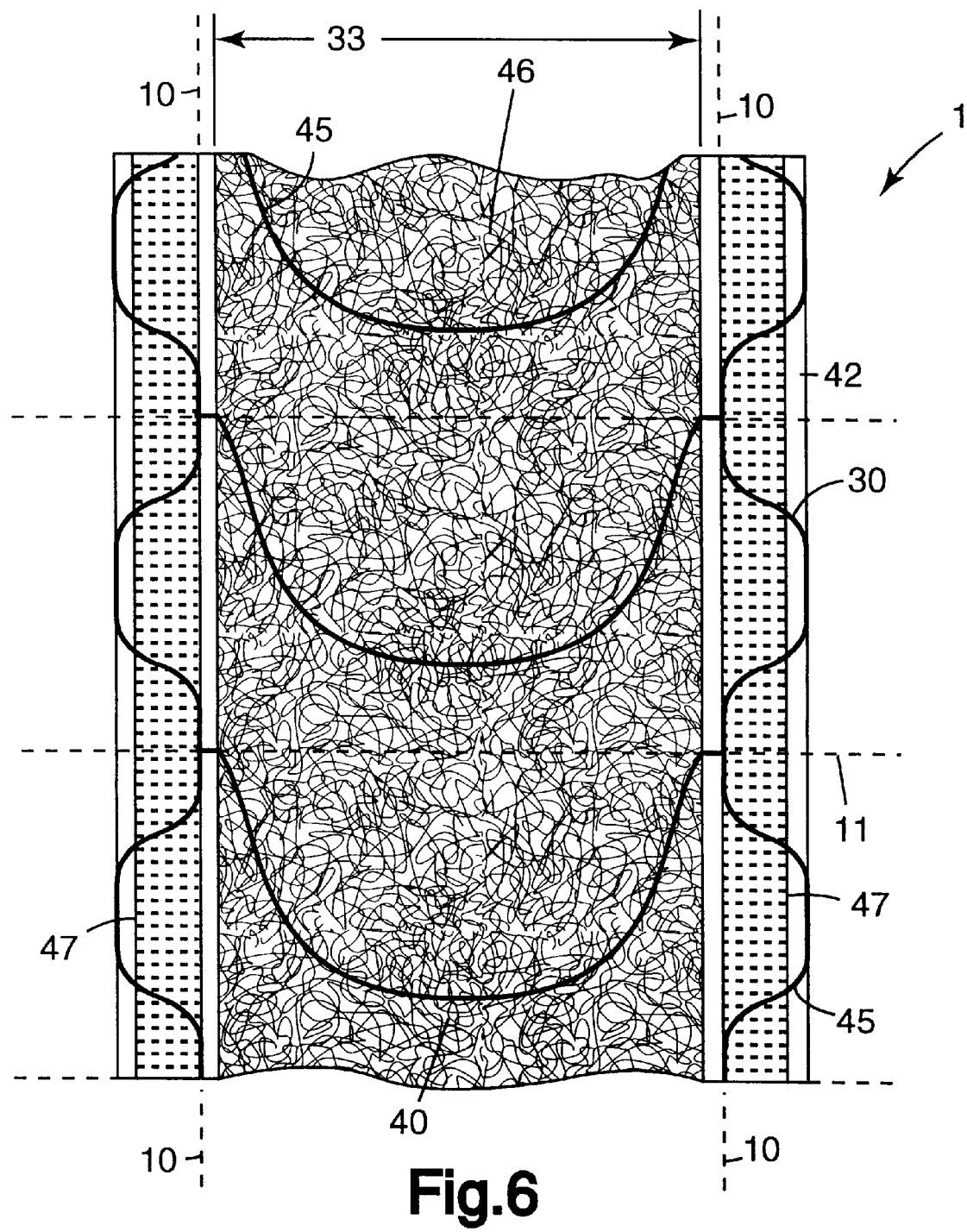

An alternative embodiment of providing the invention closure system tab elements (14) is depicted in FIG. 4, with the fastening tab portion (34) first end (37) on the terminal end portion (32) provided with smooth outer side edges (30). The closure system tab elements (14) are also cut into a slightly modified form along the cut pattern (35) by providing a region (5) where the cut line pattern slowly tapers from a portion (46) of the cut line separating two adjacent terminal end portions to an offset portion (47) of the cut line (35) separating the attachment portion from the bridging portion (38). In this embodiment, again the substantially constant length (16) of the closure tab element (14) extends across the majority of the width of the closure tab element (14) and over the entire width of the second portion (33). However, the fastening tab portion (34) or terminal end portion (32) first end (37) tapers in length. The tapered first end (37) on the terminal end portion (32) can be formed by removing a portion of the terminal end portion such as shown in FIG. 6 and/or by suitably nested cut patterns as shown in FIG. 8. The curved side edge (30) of the first end (37) eliminates or reduces the presence of sharp corners which can cause discomfort for the wearer of the disposable absorbent article if such sharp corners come in contact with the skin. The first end (37) containing the at least first fastening region hook material has an average length (36). The fastening tab portion (34) on terminal end portion (32) first end (37) is preferably provided so that no sharp corner portions extend out beyond the edge (10) of the continuous web (41) used in forming the disposable absorbent article (91). In that, the length of the closure system tab element (14) varies in the first end (37), there is a need for diverging cut lines in this region which requires waste or selvage of a certain portion of closure system web material in the first end region in this embodiment.

Figure 5:
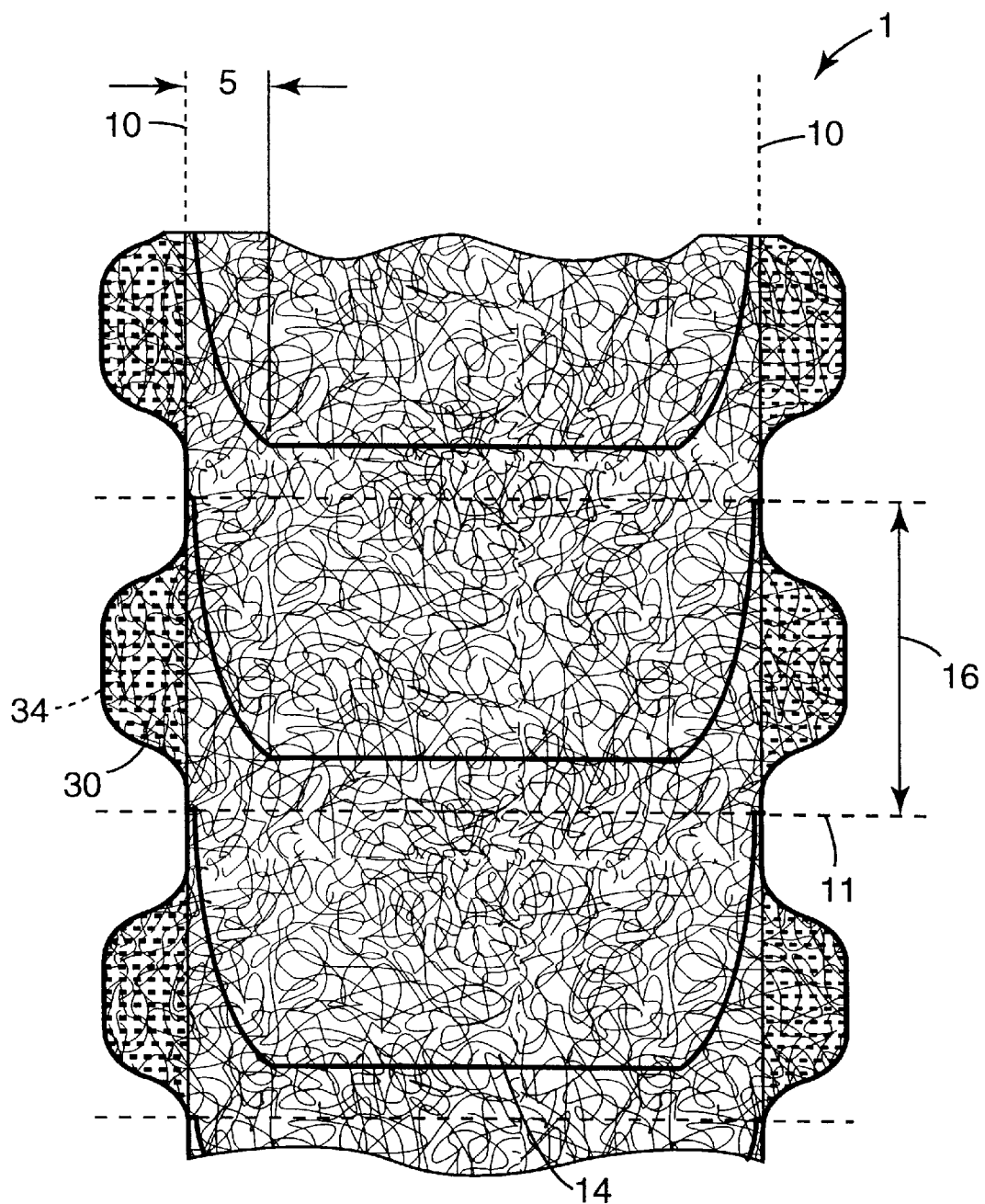
FIGS. 5–7 are top perspective views of three further embodiments of closure system webs in accordance with the present invention.

FIG. 5 depicts a variation of the FIG. 4 embodiment where the tapered region (5) of the cut pattern of the closure system web (1) has shifted outward slightly at the top portion. Also, the loop material (8) and/or the sheet of fibers has been extended outward so that it covers the entire terminal end portions, from which are formed the fastening tab portions (34).

FIG. 6 shows a further embodiment similar to that shown in FIG. 4, where there is shown a cut out region or selvage (42) to be removed from the terminal end portions of the closure system web (1). In this embodiment, the cut line (45) in the second portion (33) is in the form of a substantially continuous arc forming a generally semi-circular attachment portion (46). The bridging portion (40) interconnecting the two terminal end portions (47) is a corresponding concave structure.

Figure 7:
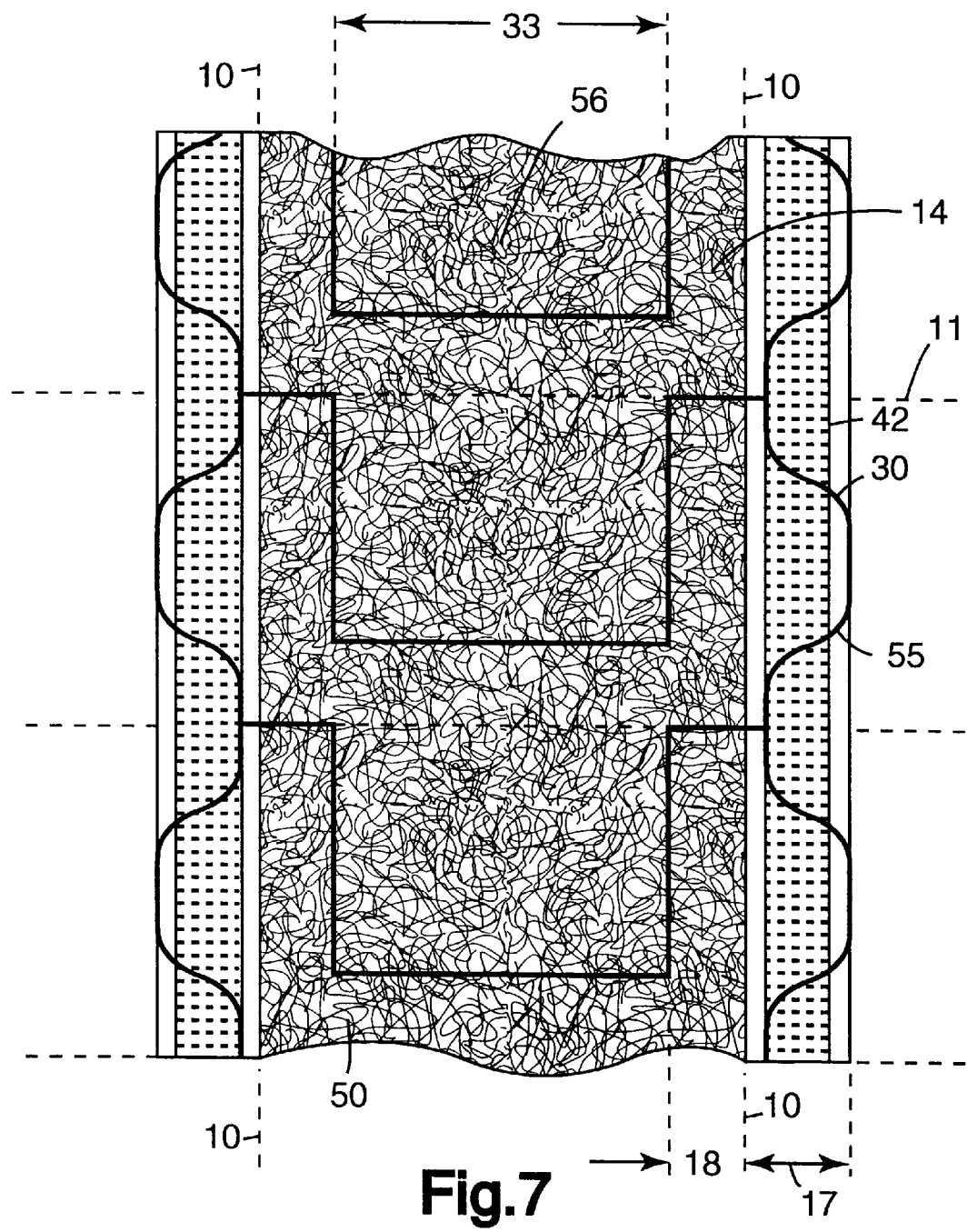

FIG. 7 illustrates a further embodiment of a closure system tab element designed in accordance with the invention wherein the attachment portion (56) is in the shape of a rectangle, also providing a rectangular bridging element or band (50) from the second portion (33). The individual closure system tab elements (14) are cut along the tab element cut line (55) providing fastening tab portions with a curved edge (30) on the first end (17) and a rectilinear second end (18).

The embodiment shown in FIG. 8 shows an alternative for producing rounded edge (30) fastening tab portion first ends on a multiple width closure system web provided with multiple terminal end portions and second portions. With the terminal end portions at the outside edges of the closure system web the fastening tab portion curved side edges (30) are still provided by removal of selvage material. However, with intermediate terminal end portions, two nested curved side edges (30) can be provided by a single sinusoidal or like undulating cut line as shown in FIG. 8. The FIG. 8 embodiment results in two secondary closure system webs (56) cut from a single multiple width primary closure system web. The two secondary closure system webs (56) can be simultaneously or subsequently cut into closure system tab elements (14), as disclosed in the other embodiments of the invention.

As shown in FIG. 8, the intermediary terminal end portions curved side edges are provided by a single sinusoidal or like undulating cut line such that the fastening tab portion first ends having the first fastening regions nest without any wasted material or selvage. However, if desired, an intermediate waste or selvage region can be provided, particularly where the first fastening region is asymmetrical across its width dimension. For example, the base of the fastening tab portion first end and/or the first fastening region can be distinct and different from the outer tip of the fastening tab portion first end. In the FIG. 8 embodiment, the curved portion of the fastening tab portion first end is symmetrical in that a continuous first fastening region is provided across the entire width of the curved portion of the fastening tab portion first end. An asymmetrical fastening tab portion first end could also be provided. For example, the first end could be provided with two distinct different attachment regions along it's width, such as a combination of a mechanical fastening region with an adhesive fastening region. Alternatively, a single region with no fastening means could be provided such as a finger lift region at the tip of the first end which region is not reciprocally provided at the base of the fastening tab portion first end. These and other asymmetrically fastening tab designs cut from a multiple width closure system web would generally require the provisions of two adjacent terminal end portions first ends in the central portion of the closure system web with separate cut lines for each to provide the desired asymmetrical fastening tab portions first ends on the two or more secondary closure system webs.

Figure 9:
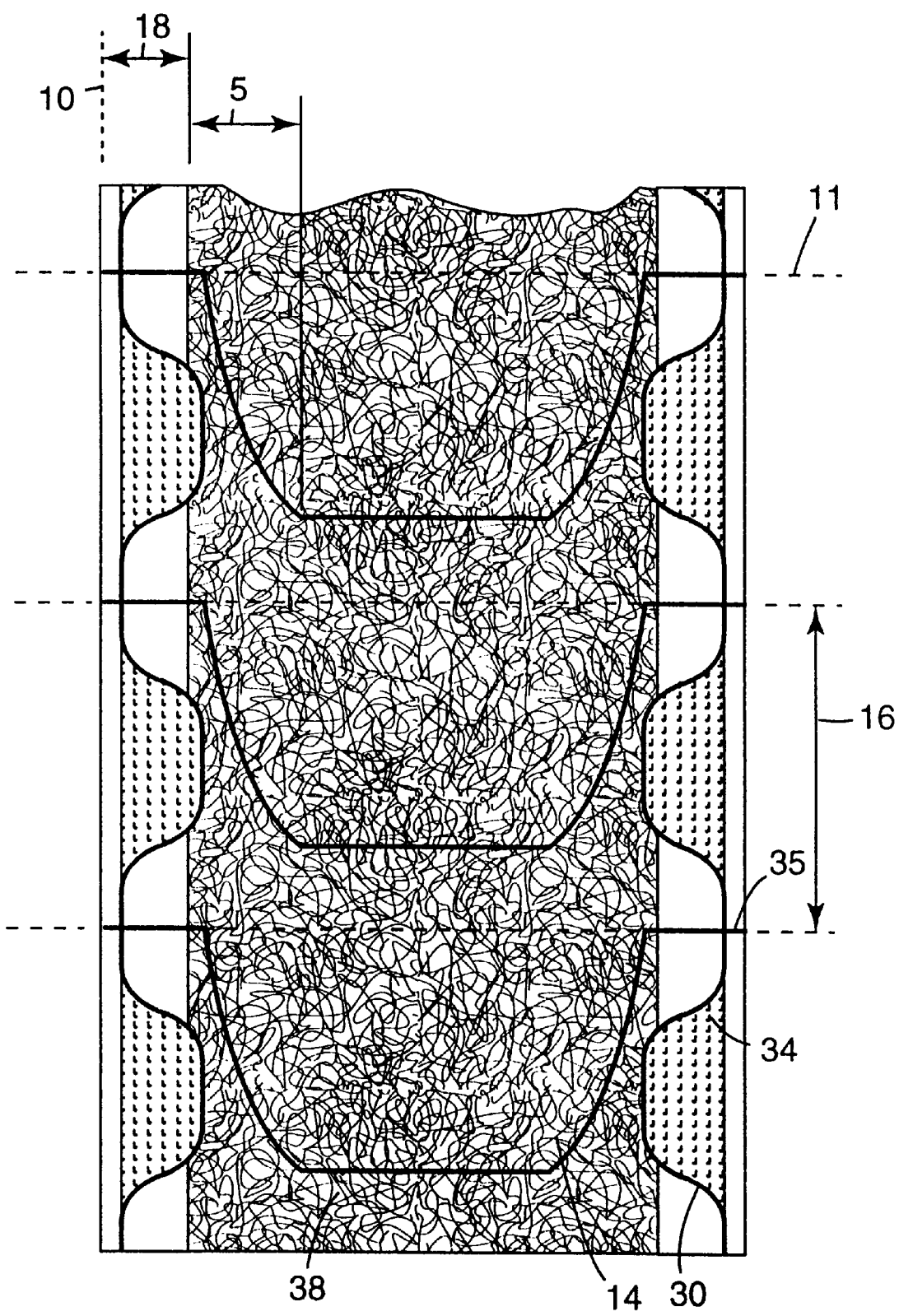
FIG. 9 is a top perspective view of a further embodiment of a closure system web in accordance with the present invention.

In the embodiment depicted in FIG. 9, the cut out fastening tab portion first end has been folded back onto the closure system web, which can be done simultaneously with or following cutting out of the closure system tab elements. The fastening tab portion first end is preferably folded along the lines separating the first end from the second end where the first end is designed to removably adhere to the mating second fastening region on the attachment portion and the second end is designed to permanently attach to the disposable absorbent article. The FIG. 9 embodiment again is exemplified using a hook and loop type mechanical fastening closure system for the first and second fastening regions.

Figure 17:
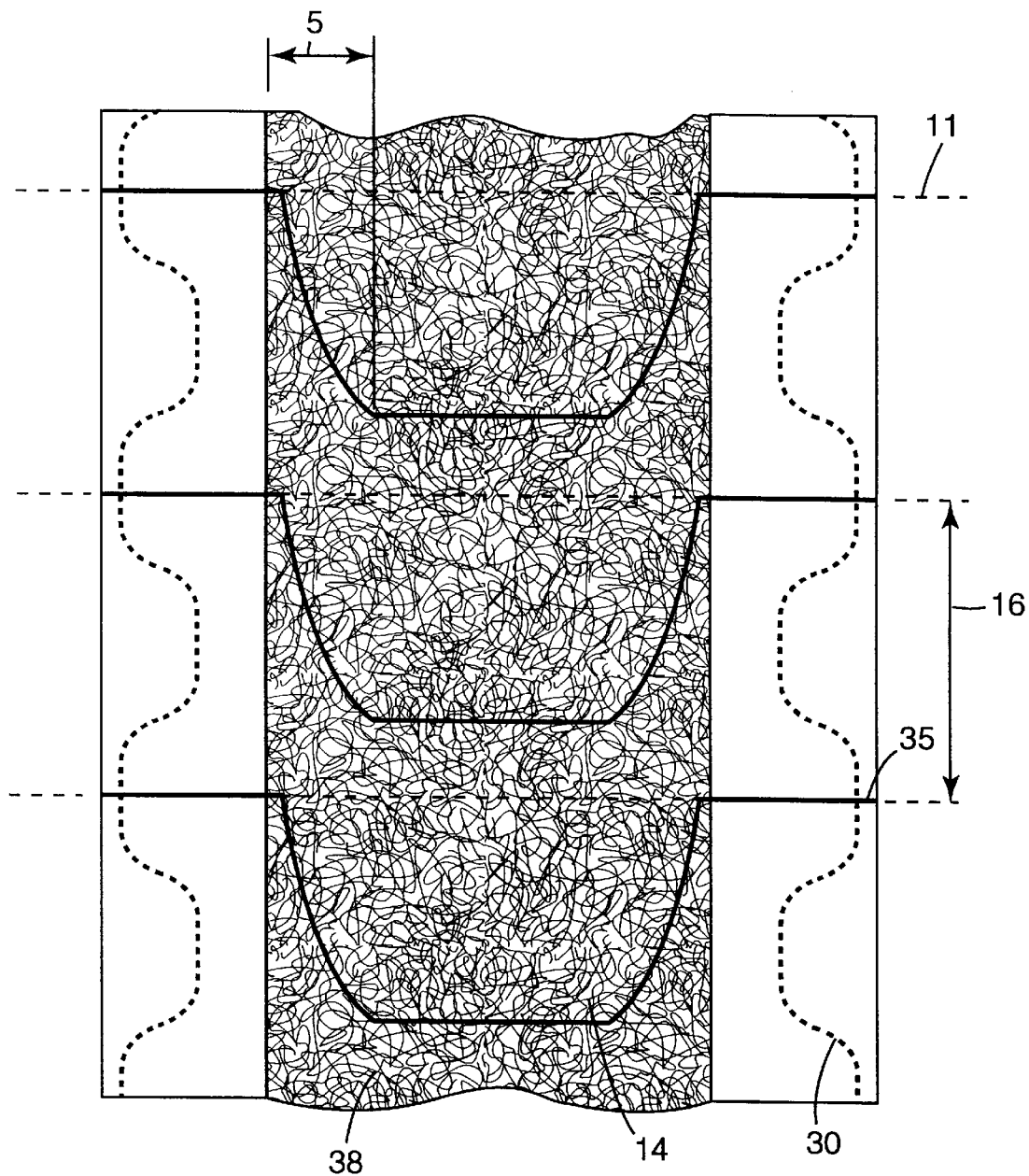
FIG. 17 is a top perspective view of a further embodiment of a closure web in accordance with the present invention.

An alternative to the FIG. 9 embodiment is shown in FIG. 17 wherein the fastening tab portion first end provided with the first fastening region is folded away from the second fastening region rather than toward it. In this case, the fold is preferably away from the line separating the fastening tab portion first end and second end. The folded portion of the fastening tab portion first end is preferably entirely within a nonfolded portion of the fastening tab portion first end. This ensures that the folded portion does not get between the backing and the disposable absorbent article when the tab element is attached.

FIG. 18 is an alternative of the invention where the tab element is in a general chevron form. This embodiment would not have a bridging element and the second portion would have a general v-shape when on the disposable absorbent article.

Figure 10:
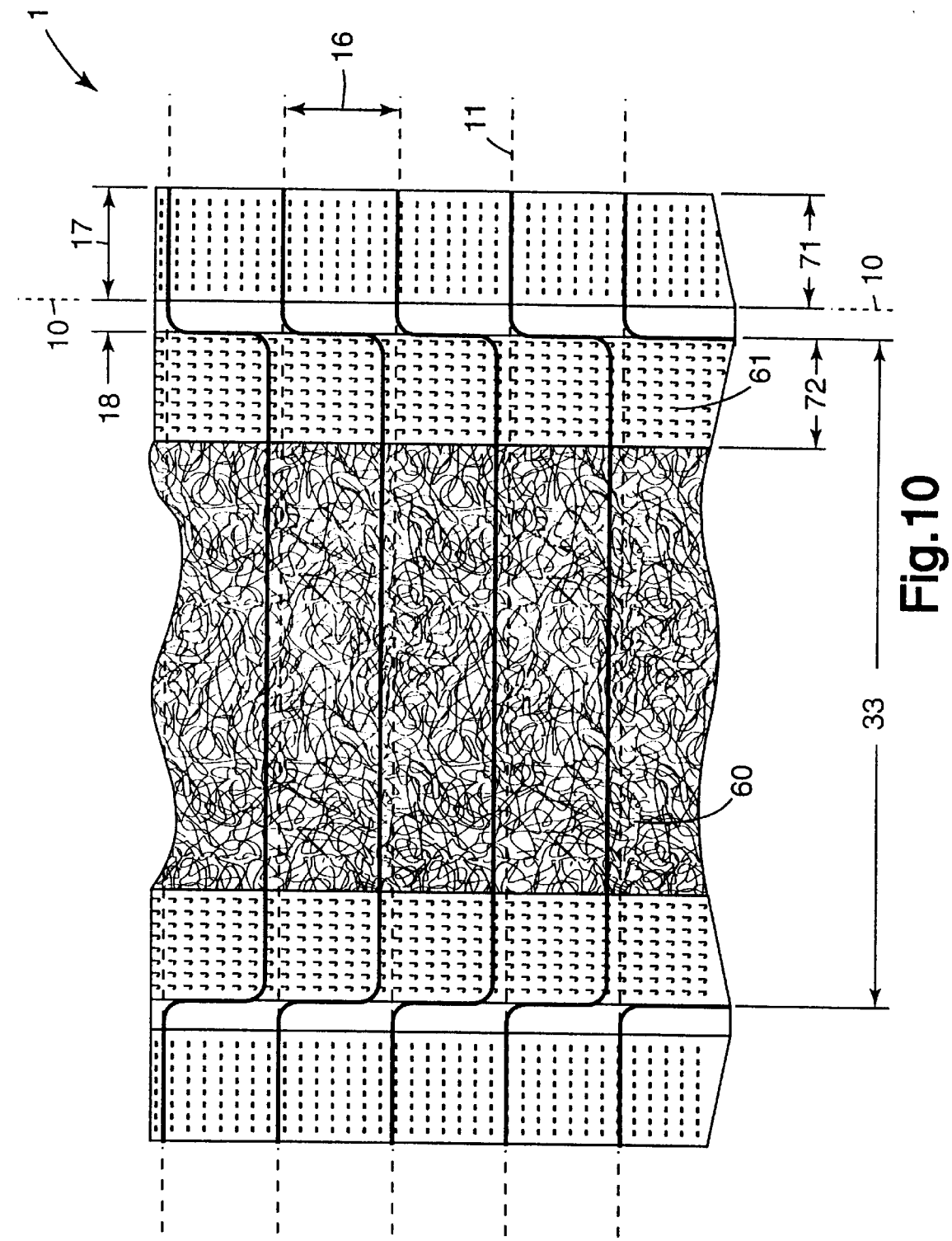
FIG. 10 is a top perspective view of a further embodiment of a closure system web in accordance with the present invention.

FIG. 10 is an alternative embodiment of the invention where two first fastening regions (71) and (72) are provided, both in this case hook mechanical fastening regions; one at the terminal end portion first end (17) and a second at the outer side margins (61) of the attachment portion (60) in the second portion (33). The first fastening region (71) provided at the terminal end portion first end (17) would be on a first face of the backing, whereas the second first fastening region (72) would be provided on a second face of the backing adjacent the attachment portion (60) on the second portion (33).

In the FIG. 10 embodiment, the two first fastening regions (71 and 72) are provided by hook mechanical fastening material with the second fastening region provided by loop mechanical fastening material which forms the attachment portion for the first fastening region (71) on the terminal end portion first end (17). The second first fastening region hook mechanical fastening material (72), provided adjacent the attachment portion (60), on the second portion (33) can be used to interengage with suitable loop or non-woven materials provided on a face of the disposable absorbent article opposite that attached to the terminal end portion or fastening tab portion second end (18). This suitable loop or non-woven material is generally located on a side edge region of the disposable absorbent article adjacent or subjacent to the region of the article attached to the second end (18) of the fastening tab portion and can be a separately applied loop material or a nonwoven topsheet type material.

Generally, in the above described embodiments, the overall shape of the closure system tab elements is a v or u, or like shape, however, other shapes are possible, including w-shapes.

FIG. 11 depicts an alternative embodiment of the invention wherein the terminal end portions are provided in a central region of a closure system web. The fastening tab portion first end on the terminal end portion is symmetrical in FIG. 11 so a single cut line can be used to form the first end curved end side edge (30) as described above relative to the FIG. 8 embodiment. The fastening tab portion is provided with a region (61) which is substantially free of fastening elements to provide a finger lift region (62). In the FIG. 11 embodiment, the two opposing closure system tab elements (63) and (64) cut from the closure system web are mirror images of each other; one providing the fastening tab portion and the attachment portion on one edge region of a disposable absorbent garment; and the opposing tab element providing an opposing fastening tab portion and an attachment portion on the opposite edge of the disposable absorbent article. With this embodiment, there are two separate and distinct attachment portions (65) and (66) and no bridging portion or band connecting the two terminal end portions or fastening tab portions.

FIG. 12 illustrates how the FIG. 11 closure system tab elements (63) and (64) would be placed on the continuous web (41) forming a portion of the disposable absorbent article providing two separate attachment portions (65) and (66) and two fastening tab portions.

Although the first fastening regions depicted in the above illustrated embodiments are provided by a mechanical fastening element, particularly a hook mechanical fastening material (4), attached to the backing (2) by a provided pressure sensitive adhesive layer (9), the first fastening region can be provided by other attachment materials or in other ways. Specifically, the first fastening region can be any suitable attachment material including hook or loop mechanical fastening materials or regions, pressure sensitive adhesive regions or patches, cohesive adhesive regions or patches, and the like. Also other mechanical fastening type materials are possible, such as snap fasteners, provided that a suitable mating engagement surface is provided on the attachment portion on the opposite face of the closure system web. Further the first fastening region can be provided as a separate element attached to the backing (2) first face as shown in the drawings or can be integrally formed with the backing (2), for example, the backing could be an extruded film material with molded hook fastening elements provided only at the terminal end portions thereof Alternatively, the first fastening region can be provided on a separate backing (6) which is attached to backing (2) by suitable methods, such as hot melt or pressure sensitive adhesives (as shown), heat or sonic welding, or other conventional means.

Where the first fastening region is provided by a pressure sensitive adhesive it is not necessary that the surface to which the first fastening region attaches be a surface provided by the second fastening region. For example, the closure system tab elements could be attached to an inside surface of a continuous backsheet web such that the first fastening region would attach to the backsheet web, or further web on a backsheet web, with the second fastening region of the closure system tab element reinforcing the backsheet web at a location where the first fastening region would attach to form a suitable tape fastening region. In this embodiment, the backing second face could be provided with a suitable pressure sensitive adhesive for attaching to the face of the, e.g., inside backsheet web. Alternatively, the backing second face could be attached to the backsheet web or a further web by other attachment methods as previously discussed.

The backing (2) for the closure system web (1) can be any suitable web product or laminate including film materials, foam products, fabrics, such as woven or non-woven webs, or multi-layer structures comprising any or all of the above-mentioned materials and the like, which multi-layer structuring can be either continuous or intermittent across the length and/or width of the backing (2). The backing (2 or 82) could be an elastic material with specific elastic region, such as (81) depicted in FIG. 13. This elastic region (81) can be provided by specifically elasticating a region of the backing (2 or 82). In FIG. 13, the elastic backing (82) is formed as described in U.S. Pat. No. 5,505,852 which discloses a coextruded inelastic multilayer film having elastic (86) and inelastic layers (85 and 87) which multilayer film can be selectively stretch activated to create an elastic, e.g., by selectively stretching in region (81) in the manner disclosed in U.S. Pat. No. 5,505,852. However, alternatively, the entire backing (2 or 82) can be made elastic such as by providing an elastomeric film or an elastomeric woven or non-woven material, or laminates thereof, as the backing (2 or 82). In FIG. 13, the hook fastening material (4) is attached to an inelastic portion of the backing (82) by an adhesive layer (89) which could be provided or coated on the hook material (4) or on the backing (82).

An alternative method of providing a zone of elasticity (81) on a film backing is shown in FIG. 15. In FIG. 15, the film backing is formed by selective side by side elastic and inelastic regions, for example, by side by side coextrusion of elastic and inelastic materials as disclosed in Japanese Appln. No. 8-187113.

Alternatively, a side-by-side elastic and inelastic region could be provided by included elastic regions within an inelastic matrix as disclosed in U.S. Pat. No. 5,429,856.

An elastic backing material (12 or 82) can also be selectively bonded or laminated to an inelastic film or other web material in an unextended state followed by selective stretching of the composite to provide elasticity as disclosed in U.S. Pat. Nos. 5,167,897; 5,156,793; 5,143,679; or 5,527,304, or PCT WO 96/1048 (stretching is facilitated by selectively slitting the inelastic layer) or an elastic material can be applied to a separate backing layer (e.g., a non-woven web) in a stretched state either by intermittent or continuous attachment so as to allow the elastic material to recover resulting in the laminate backing material of the laminate backing so formed gather or buckle between attachment points forming an elastic composite in that region. Separately applied elastic material can also be applied to either the first or the second face of another continuous backing material which can also be elastic or inelastic, which other continuous backing could be stretched, unstretched or gathered, or corrugated when attached to the elastic material.

The loop materials (8) or (88) can be any conventional woven or non-woven loop material which is suitably attached to the backing (2) or (82) as would be known in the art.

FIG. 14 shows an alternative embodiment of the invention where a loop fabric is selectively provided to be engagable with a hook material in region (83) and generally less engagable with the hook material in region (84). Loop fabric is applied to a film backing (82). This can be accomplished by taking a relatively low loft non-woven type fabric and causing it to selectively gather or corrugate in region (81) and be substantially flat in region (84) which region (84) can further be consolidated as required. This can be accomplished by using the method depicted in FIG. 3 by selectively providing corrugations or undulations in the web (3) only in the region or the second portion forming the attachment portion on the second face of the closure system web. Suitable non-woven materials for forming the loop material are disclosed, for example, in U.S. Pat. Nos. 5,256,231; 5,614,281; 5,032,122; 5,470,417; 5,326,612, and WO 96/04812, WO 95/33390.

FIG. 15 shows an alternative embodiment where a backing (107) is side-by-side coextruded to have inelastic regions (104 and 106) on either side of an elastic region (105). Further, an inelastic region (106) are formed integral hook elements. An inextensible web (103) is attached to first face of the backing and in at least elastic region (81) is corrugated by the method shown in FIG. 3 or otherwise compressed in its width dimension as is shown in the art. On the second face of the backing is provided a loop material (108) which is shown as corrugated by the method shown in FIG. 3 across its full width allowing the elastic region (8) to elongate and provide a substantially loop attachment portion.

The invention further provides a method of forming a closure system for a disposable absorbent article comprising the steps of, providing at least one continuous or substantially continuous web capable of forming a portion of a disposable absorbent article. This web has at least a first width dimension defining two side edges and an indefinite length dimension. A closure system web is also provided comprising at least one backing having a first face and a second face. The closure system web has a second width dimension greater than the first width dimension and an indefinite length. The first face of the closure system web is provided with at least one first fastening region at at least one terminal end portion of the closure system web. At least one second fastening region is provided on the second face of the closure system web in at least the second portion adjacent the terminal end portion provided with the first fastening region. Closure system tab elements are cut from the closure system web which tab elements have a definite length dimension. The closure system tab elements have at least one fastening tab portion, comprising the at least one first fastening region on the terminal end portion, and an attachment portion comprising the second portion having the second fastening region.

The closure system tab elements are then attached to the at least one continuous or substantially continuous web at regular spaced intervals in the indefinite length dimension in a continuous manner forming a second continuous web. The second continuous web is then cut along transverse cut lines in the indefinite length dimension. The cut lines are such that they bisect the closure system tab elements along the tab element definite length dimension, so that the fastening tab portion is on a first side of the cut line and the attachment portion is on a second opposing side of the cut line. This provides fastening tab portions on a first end of one absorbent article and an attachment portion on a second end of an adjacent absorbent article. Preferably the transverse cut line also forms the discrete absorbent article.

We claim:

1. A closure system for a disposable absorbent article comprising a disposable absorbent article having a first width dimension defining two side edges and two end edges, a closure system comprising:

(a) at least one fastening tab, and a least one attachment portion, said at least one fastening tab and said at least one attachment portion being located at opposing ends of the disposable absorbent article, said at least one fastening tab having a backing having a first face and a second face and a top edge and a bottom edge the first face being provided with at least one first fastening region at at least a first end, and (b) at least one second fastening region on said at least one attachment portion the at least one attachment portion having a backing, a top edge and a bottom edge, at least a discrete edge portion of the at least one attachment portion top edge being laterally coextensive with a discrete edge portion of the at least one fastening tab bottom edge wherein at least at an area adjacent the two discrete edge portions, of the at least one fastening tab and the attachment portion, the respective attachment portion and fastening tab backings are identical.

2. The closure system of claim 1 wherein the at least one fastening tab bottom edge is coextensive with a portion of a first end edge of the disposable absorbent article.

3. The closure system of claim 2, wherein the at least one attachment portion top edge is coextensive with a portion of a second end edge of the disposable absorbent article.

4. The closure system of claim 1 wherein the at least one first fastening tab portion attached to the absorbent article has a first end extending outwardly beyond the side edges of the absorbent article and a second end attached to the absorbent article, at least the first end having said first fastening region.

5. The closure system of claim 4 wherein the first fastening region is a hook mechanical fastener on the first end of the fastening tab portion with the second end of the fastening tab portion on the first face having a mating loop material for temporary attachment of the hook mechanical fastener prior to use.

6. The closure system of claim 5 wherein the fastening tab backing is an elastic film.

7. The closure system of claim 4 wherein the fastening tab second end has a minimum width of from 1 to 5 cm.

8. The closure system of claim 4 wherein the attachment portion average length is from 60 to 90 percent of the average length of the first fastening region.

9. The closure system of claim 4 wherein the at least one fastening tab portion comprises two fastening tab portions which are connected by a bridging portion, at least a portion of the bridging portion forming the coextensive discrete edge portion of the at least one fastening tab coextensive with the second top edge of the disposable absorbent article.

10. The closure system of claim 9 wherein the bridging portion has an average length less than average length of the attachment portion.

11. The closure system of claim 9 wherein the two fastening tabs and the bridging portion are in a general u-shape.

12. The closure system of claim 10 wherein the average width of the bridging portion is greater than the average width of the attachment portion.

13. The closure system of claim 10 wherein the average length of the bridging portion is less than 30 percent of the average length of the attachment portion.

14. The closure system of claim 13 wherein the bridging portion and the attachment portion are identical laminate structures.

15. The closure system of claim 14 wherein the bridging portion is a negative inverted mirror image of the attachment portion such that the two portions if combined would form a rectangular portion.

16. The closure system of claim 1 wherein the first fastening region comprises a pressure sensitive adhesive patch.

17. The closure system of claim 16 wherein the first fastening region pressure sensitive adhesive patch is provided on the at least one backing.

18. The closure system of claim 17 wherein the first fastening region pressure sensitive adhesive patch is provided on a tape backing first face with the second face attached to the at least one fastening tab backing.

19. The closure system of claim 1 wherein the first fastening region comprises a mechanical fastening patch and the second fastening region on the attachment portion comprises a mating mechanical fastening patch wherein a face of the backing of the attachment portion is attached to an outer surface of the disposable absorbent article and an opposite face of the backing is provided with the mating mechanical fastening patch.

20. The closure system of claim 19 wherein the mechanical fastening patch comprises a hook mechanical fastening patch and the mating mechanical fastening patch comprises a loop mechanical fastening patch.

21. The closure system of claim 20 wherein the hook mechanical fastener patch comprises a backing having hook mechanical fastening elements projecting from a first face and a second face attached to the at least one fastening tab backing.

22. The closure system of claim 20 wherein the loop mechanical fastening patch comprises the attachment portion backing.

23. The closure system of claim 20 wherein the loop mechanical fastening patch is a loop fabric attached to the attachment portion backing.

24. The closure system of claim 1 wherein the first face of the at least one fastening tab backing is provided with a pressure sensitive adhesive for attachment of the at least one fastening tab to the disposable absorbent article.

25. The closure system of claim 1 wherein at least the fastening tab portions are provided with elastic regions.

26. The closure system of claim 25 wherein the elastic regions are adjacent the first fastening region.

27. The closure system of claim 26 wherein the elastic region is on the first end of the fastening tab portion adjacent the side edge, and outboard, of the disposable absorbent article.

28. The closure system of claim 26 wherein the elastic region is provided by laminating an elastic sheet to the fastening tab and/or attachment portion backing.

29. The closure system of claim 1 wherein there are two separate attachment portions.

30. The closure system of claim 1 wherein the attachment portion backing is at least in part elastic.

31. The closure system of claim 1 wherein the fastening tab backing is at least in part elastic.

32. The closure system of claim 31 wherein the attachment portion backing is an elastic film.

33. The closure system of claim 1 wherein the attachment portion is at least in part inelastic.

34. The closure system of claim 33 wherein the attachment portion backing is at least in part inextensible.

35. The closure system of claim 1 wherein the attachment portion backing is a laminate of a film layer and a nonwoven material.

36. The closure system of claim 1 wherein the maximum length of the fastening tab is from 2 to 10 cm.

37. The closure system of claim 1 wherein the fastening tab maximum length is from 2 to 6 cm.

38. The closure system of claim 1 wherein the fastening tab first fastening region is on average from 0.3 to 5 cm long.

39. The closure system of claim 1 wherein the fastening tab first fastening region has a cross sectional area of from 1 to 10 cm$^2$.

40. The closure system of claim 1 wherein the attachment portion average length is from 40 to 95 percent of the average length of the first fastening region.

* * * * *

UNITED STATES PATENT AND TRADEMARK OFFICE
CERTIFICATE OF CORRECTION

PATENT NO. : 6,195,850 B1
DATED : March 6, 2001
INVENTOR(S) : Melbye, William L.

It is certified that error appears in the above-identified patent and that said Letters Patent is hereby corrected as shown below:

Column 2,
Line 21, after "the belt can be", insert -- reused --.

Column 12,
Line 53, after "end portions thereof", please insert -- . --.

Signed and Sealed this

First Day of October, 2002

Attest:

JAMES E. ROGAN
Attesting Officer
Director of the United States Patent and Trademark Office